(12) United States Patent
Samaniego et al.

(10) Patent No.: US 10,617,526 B2
(45) Date of Patent: Apr. 14, 2020

(54) COMPOSITE BONE CONSTRUCTS AND METHODS

(71) Applicant: AlloSource, Centennial, CO (US)

(72) Inventors: Adrian C. Samaniego, Highlands Ranch, CO (US); Matthew J. Southard, Denver, CO (US); Kenneth Blood, Littleton, CO (US); Richard Dempsey, Centennial, CO (US)

(73) Assignee: ALLOSOURCE, Centennial, CO (US)

( * ) Notice: Subject to any disclaimer, the term of this patent is extended or adjusted under 35 U.S.C. 154(b) by 272 days.

(21) Appl. No.: 15/676,305

(22) Filed: Aug. 14, 2017

(65) Prior Publication Data

US 2017/0367826 A1 Dec. 28, 2017

Related U.S. Application Data

(63) Continuation of application No. 14/713,627, filed on May 15, 2015, now Pat. No. 9,730,796.

(60) Provisional application No. 61/994,674, filed on May 16, 2014.

(51) Int. Cl.
*A61F 2/28* (2006.01)
*A61L 27/44* (2006.01)
*A61L 27/48* (2006.01)

(52) U.S. Cl.
CPC ............... *A61F 2/28* (2013.01); *A61L 27/44* (2013.01); *A61L 27/48* (2013.01); *A61F 2002/2835* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,627,853 A | 12/1986 | Campbell et al. |
| 4,963,151 A | 10/1990 | Ducheyne et al. |
| 5,073,373 A | 12/1991 | O'Leary et al. |
| 5,284,655 A | 2/1994 | Bogdansky et al. |
| 5,314,476 A | 5/1994 | Prewett et al. |
| 5,405,390 A | 4/1995 | O'Leary et al. |
| 5,439,684 A | 8/1995 | Prewett et al. |
| 5,507,813 A | 4/1996 | Dowd et al. |
| 5,510,396 A | 4/1996 | Prewett et al. |
| 5,531,791 A | 7/1996 | Wolfinbarger |
| 5,556,379 A | 9/1996 | Wolfinbarger |
| 5,676,146 A | 10/1997 | Scarborough |
| 5,707,962 A | 1/1998 | Chen et al. |
| 5,749,874 A | 5/1998 | Schwartz |
| 5,769,899 A | 6/1998 | Schwartz et al. |
| 5,788,941 A | 8/1998 | Dalmasso et al. |
| 5,797,871 A | 8/1998 | Wolfinbarger |
| 5,820,581 A | 10/1998 | Wolfinbarger |
| 5,895,426 A | 4/1999 | Scarborough et al. |
| 5,948,428 A | 9/1999 | Lee et al. |
| 5,972,368 A | 10/1999 | McKay |
| 5,976,104 A | 11/1999 | Wolfinbarger |
| 5,977,034 A | 11/1999 | Wolfinbarger |
| 5,977,432 A | 11/1999 | Wolfinbarger |
| 6,024,735 A | 2/2000 | Wolfinbarger |
| 6,090,998 A | 7/2000 | Grooms et al. |
| 6,180,606 B1 | 1/2001 | Chen et al. |
| 6,189,537 B1 | 2/2001 | Wolfinbarger |
| 6,200,347 B1 | 3/2001 | Anderson et al. |
| 6,214,369 B1 | 4/2001 | Grande |
| 6,294,041 B1 | 9/2001 | Boyce et al. |
| 6,305,379 B1 | 10/2001 | Wolfinbarger |
| 6,315,795 B1 | 11/2001 | Scarborough et al. |
| 6,340,477 B1 | 1/2002 | Anderson |
| 6,371,988 B1 | 4/2002 | Pafford et al. |
| 6,436,138 B1 | 8/2002 | Dowd |
| 6,464,983 B1 | 10/2002 | Grotendorst |
| 6,478,825 B1 | 11/2002 | Winterbottom et al. |
| 6,482,231 B1 | 11/2002 | Abatangelo |
| 6,482,233 B1 | 11/2002 | Aebi et al. |
| 6,511,509 B1 | 1/2003 | Ford et al. |
| 6,576,015 B2 | 6/2003 | Geistlich et al. |
| 6,616,698 B2 | 9/2003 | Scarborough |
| 6,652,593 B2 | 11/2003 | Boyer, II et al. |
| 6,685,626 B2 | 2/2004 | Wironen |
| 6,696,073 B2 | 2/2004 | Boyce et al. |
| 6,716,245 B2 | 4/2004 | Pasquet et al. |
| 6,746,484 B1 | 6/2004 | Liu et al. |
| 6,800,480 B1 | 10/2004 | Bodnar et al. |
| 6,805,713 B1 | 10/2004 | Carter et al. |
| 6,837,907 B2 | 1/2005 | Wolfinbarger |
| 6,855,169 B2 | 2/2005 | Boyer et al. |

(Continued)

FOREIGN PATENT DOCUMENTS

| | | |
|---|---|---|
| WO | 2012135205 | 10/2012 |
| WO | 2013047936 | 4/2013 |
| WO | 2015175983 A1 | 11/2015 |

OTHER PUBLICATIONS

International Preliminary Report on Patentability for PCT application No. PCT/US2015/031160 filed May 15, 2015, dated Dec. 1, 2016, 8 pages.

(Continued)

*Primary Examiner* — Robert A Wax
*Assistant Examiner* — Randeep Singh
(74) *Attorney, Agent, or Firm* — Kilpatrick Townsend & Stockton

(57) ABSTRACT

Embodiments of the present technology include a method of making a bone composite graft for administration to a patient. The method may include combining a human cadaveric bone material with a plurality of polymethyl methacrylate binder particles and spincasting the combined human cadaveric bone material and polymethyl methacrylate binder particles to produce the bone composite graft. The method may also include ablating the bone composite graft to increase the surface area of bone material exposed. The human cadaveric bone material may be immobilized in the plurality of polymethyl methacrylate binder particles. The human cadaveric bone material may be present in an amount that is 50 weight percent of the bone composite graft, or less. Additionally, the bone composite graft may have a yield strength that is at least 13,000 N/cm2 and no greater than 15,000 N/cm2.

37 Claims, 5 Drawing Sheets

(56) References Cited

U.S. PATENT DOCUMENTS

| | | |
|---|---|---|
| 6,902,578 B1 | 6/2005 | Anderson et al. |
| 6,911,045 B2 | 6/2005 | Shimp |
| 6,911,212 B2 | 6/2005 | Gertzman et al. |
| 7,018,412 B2 | 3/2006 | Ferreira et al. |
| 7,048,765 B1 | 5/2006 | Grooms et al. |
| 7,115,146 B2 | 10/2006 | Boyer, II et al. |
| 7,132,110 B2 | 11/2006 | Kay et al. |
| 7,163,691 B2 | 1/2007 | Knaack et al. |
| 7,172,629 B2 | 2/2007 | McKay |
| 7,241,874 B2 | 7/2007 | Thorne |
| 7,297,540 B2 | 11/2007 | Mitrani |
| 7,316,822 B2 | 1/2008 | Binette et al. |
| 7,323,011 B2 | 1/2008 | Shepard et al. |
| 7,335,381 B2 | 2/2008 | Malinin |
| 7,371,409 B2 | 5/2008 | Petersen et al. |
| 7,498,040 B2 | 3/2009 | Masinaei et al. |
| 7,582,309 B2 | 9/2009 | Rosenberg et al. |
| 7,608,113 B2 | 10/2009 | Boyer et al. |
| 7,622,562 B2 | 11/2009 | Thorne et al. |
| 7,662,185 B2 | 2/2010 | Alfaro et al. |
| 7,753,963 B2 | 7/2010 | Boyer et al. |
| 7,785,634 B2 | 8/2010 | Borden |
| 7,807,458 B2 | 10/2010 | Schiller |
| 7,811,608 B2 | 10/2010 | Kay et al. |
| 7,815,926 B2 | 10/2010 | Syring et al. |
| 7,837,740 B2 | 11/2010 | Semler et al. |
| 7,875,296 B2 | 1/2011 | Binette et al. |
| 7,879,103 B2 | 2/2011 | Gertzman et al. |
| 7,883,511 B2 | 2/2011 | Fernyhough |
| 7,931,692 B2 | 4/2011 | Sybert et al. |
| 8,002,813 B2 | 8/2011 | Scarborough et al. |
| 8,002,837 B2 | 8/2011 | Stream et al. |
| 8,021,692 B2 | 9/2011 | Hiles |
| 8,025,896 B2 | 9/2011 | Malaviya et al. |
| 8,039,016 B2 | 10/2011 | Drapeau et al. |
| 8,137,702 B2 | 3/2012 | Binette et al. |
| 8,163,549 B2 | 4/2012 | Yao et al. |
| 8,167,943 B2 | 5/2012 | Carter et al. |
| 8,197,474 B2 | 6/2012 | Scarborough et al. |
| 8,202,539 B2 | 6/2012 | Behnam et al. |
| 8,268,008 B2 | 9/2012 | Betz et al. |
| 8,292,968 B2 | 10/2012 | Truncale et al. |
| 8,328,876 B2 | 12/2012 | Behnam et al. |
| 8,343,229 B2 | 1/2013 | Coale |
| 8,389,017 B1 | 3/2013 | Starling et al. |
| 8,399,010 B2 | 3/2013 | McKay |
| 8,403,991 B2 | 3/2013 | Ullrich, Jr. et al. |
| 8,409,623 B2 | 4/2013 | Shim et al. |
| 8,435,566 B2 | 5/2013 | Behnam et al. |
| 8,496,970 B2 | 7/2013 | Binette et al. |
| 8,506,632 B2 | 8/2013 | Ganem et al. |
| 8,551,176 B2 | 10/2013 | Ullrich, Jr. et al. |
| 8,563,040 B2 | 10/2013 | Marchosky |
| 8,574,825 B2 | 11/2013 | Shelby et al. |
| 8,585,766 B2 | 11/2013 | Ullrich, Jr. et al. |
| 8,722,075 B2 | 5/2014 | Shimp et al. |
| 8,771,368 B2 | 7/2014 | McKay |
| 8,859,007 B2 | 10/2014 | Carter et al. |
| 8,992,964 B2 | 3/2015 | Shelby et al. |
| 9,029,077 B2 | 5/2015 | Song et al. |
| 9,744,266 B2 | 8/2017 | Stilwell et al. |
| 2003/0036800 A1 | 2/2003 | Meredith |
| 2003/0180344 A1* | 9/2003 | Wise ................ A61L 27/443 424/423 |
| 2004/0146543 A1 | 7/2004 | Shimp et al. |
| 2006/0015184 A1 | 1/2006 | Winterbottom et al. |
| 2007/0185231 A1 | 8/2007 | Liu et al. |
| 2008/0058953 A1 | 3/2008 | Scarborough |
| 2008/0249632 A1 | 10/2008 | Stone et al. |
| 2008/0249638 A1 | 10/2008 | Asgari |
| 2008/0305145 A1 | 12/2008 | Shelby et al. |
| 2010/0131064 A1 | 5/2010 | Redepenning |
| 2010/0168869 A1 | 7/2010 | Long et al. |
| 2010/0196333 A1 | 8/2010 | Gaskins et al. |
| 2010/0241228 A1 | 9/2010 | Syring et al. |
| 2011/0070271 A1 | 3/2011 | Truncale et al. |
| 2012/0082704 A1 | 4/2012 | Phillips et al. |
| 2012/0213859 A1 | 8/2012 | Shelby et al. |
| 2012/0245703 A1 | 9/2012 | Meredith |
| 2012/0251609 A1 | 10/2012 | Huang et al. |
| 2013/0189338 A1 | 7/2013 | Drapeau et al. |
| 2014/0093543 A1 | 4/2014 | Morreale |
| 2014/0121772 A1 | 5/2014 | Emerton et al. |
| 2014/0170232 A1 | 6/2014 | Shelby et al. |
| 2014/0205674 A1 | 7/2014 | Wei |
| 2014/0208980 A1 | 7/2014 | Song et al. |
| 2014/0212471 A1 | 7/2014 | Drapeau et al. |
| 2014/0212499 A1 | 7/2014 | Cooper et al. |
| 2014/0220142 A1 | 8/2014 | Song et al. |
| 2014/0242125 A1* | 8/2014 | Atala ................ A61K 35/34 424/400 |
| 2014/0255506 A1 | 9/2014 | Behnam et al. |
| 2014/0314822 A1 | 10/2014 | Carter et al. |
| 2014/0342013 A1 | 11/2014 | He et al. |
| 2015/0004247 A1 | 1/2015 | Carter et al. |
| 2015/0012107 A1 | 1/2015 | Koford et al. |
| 2015/0174295 A1 | 6/2015 | Woodell-May et al. |
| 2015/0182667 A1 | 7/2015 | Guelcher et al. |
| 2015/0202345 A1 | 7/2015 | Shelby et al. |
| 2015/0202346 A1 | 7/2015 | Shelby et al. |
| 2015/0258244 A1 | 9/2015 | Shelby et al. |
| 2015/0328003 A1 | 11/2015 | Samaniego et al. |

OTHER PUBLICATIONS

International Search Report and Written Opinion for PCT application No. PCT/US2015/031160 filed May 15, 2015, dated Aug. 18, 2015, 12 pages.

* cited by examiner

COMPOSITE BONE CONSTRUCTS AND METHODS

CROSS-REFERENCES TO RELATED APPLICATIONS

This application is a continuation of commonly assigned U.S. patent application Ser. No. 14/713,627 filed May 15, 2015, which claims the benefit of priority to U.S. Provisional Patent Application No. 61/994,674 filed May 16, 2014, the entire content of which is incorporated herein by reference for all purposes.

BACKGROUND

Embodiments of the present technology are directed in general to the field of medical grafts, and in particular to bone graft compositions, and methods of their use and manufacture.

Medical grafting procedures often involve the implantation of autogenous, allograft, or synthetic grafts into a patient to treat a particular condition or disease. The use of musculoskeletal allograft tissue in reconstructive orthopedic procedures and other medical procedures has markedly increased in recent years, and millions of musculoskeletal allografts have been safely transplanted. A common allograft is bone. Typically, bone grafts are resorbed and replaced with the patient's natural bone upon healing. Bone grafts can be used in a variety of indications, including neurosurgical and orthopedic spine procedures for example. In some instances, bone grafts can be used to fuse joints or to repair broken bones.

Allograft and autogenous bone are both derived from humans; the difference is that allograft is harvested from an individual (e.g., donor) other than the one (e.g., patient) receiving the graft. Allograft is often taken from donated cadavers so that their bone can be used for living people who are in need of the bone, for example, patients whose bones have degenerated from cancer. Such tissues represent a gift from the donor or the donor family to enhance the quality of life for other people.

Hence, bone graft compositions and methods are presently available and provide real benefits to patients in need thereof. Yet many advances may still be made to provide improved bone graft systems and methods for treating patients. The bone graft systems and treatment and manufacture methods described herein provide further solutions and answers to these outstanding needs.

BRIEF SUMMARY

Often, in recovering bone and other tissue from a donor, bone particles or dust is generated while cutting bone. These bone particles are normally considered waste and are discarded, providing no benefit to patients and limiting the reach of the donor's gift. Embodiments of the present technology may provide a way to use these bone particles and maximize the benefit and reach of a donor's gift. Additionally, embodiments of the present technology may provide a bone graft with desirable characteristics. These bone grafts may have sufficient strength to substitute or supplement natural bone, while possessing flexibility and other mechanical properties similar to natural bone. The bone grafts may be machined or formed into shapes that can be more easily implanted into a patient. Embodiments may also provide the advantage of forming a bone graft that is actually larger in size than the bone from which the bone particles come. Furthermore, embodiments may also provide for consistent properties across the graft, and the ability to tailor properties of the bone graft by adjusting processing parameters.

In a first aspect, embodiments of the present technology include a graft for administration at a treatment site of a patient. The graft may include a human cadaveric bone material immobilized in a polymeric binder. The human cadaveric bone material may include demineralized bone particles. The demineralized bone particles may have an average diameter less than 1.1 mm, less than 750 µm, less than 500 µm, or less than 250 µm. The human cadaveric bone material may include non-demineralized bone, cancellous bone, and/or cortical bone in embodiments. In some embodiments, bone from animals other than humans may be used, and the patient may be an animal other than a human.

The polymeric binder may promote cohesion between bone material with or without forming a bond between the polymer and the bone material. In embodiments, the polymeric binder may be polylactic acid, cyano acrylate (e.g., Super Glue®), diphenylmethane diisocyanate, polymethyl methacrylate (PMMA), silicones, polyurethanes, or epoxies. In some embodiments, the polymeric binder may be a surgical glue or a bone cement. The polymeric binder may dissolve or may not dissolve in a human body. The bone graft may exclude a cross-linking agent. Additionally, the bone graft may include a polymer that is not cross-linked with a cross-linking agent. The polymeric binder may exclude a cross-linking agent.

In the graft, the demineralized bone particles may be present in an amount between about 10 weight percent and about 70 weight percent, between about 10 weight percent and about 20 weight percent, between about 20 weight percent and about 30 weight percent, between about 30 weight percent and about 40 weight percent, between about 40 weight percent and about 50 weight percent, between about 50 weight percent and about 60 weight percent, or between about 60 weight percent and about 70 weight percent.

In some embodiments, the bone graft may have a compressive modulus greater than 7.0 GPa, greater than 7.5 GPa, greater than 8.0 GPa, or greater than 8.5 GPa. The yield strength of the bone graft may be greater than 10,000 N, greater than 11,000 N, greater than 12,000 N, greater than 13,000 N, greater than 14,000 N, or greater than 15,000 N. Such compressive modulus and yield strengths may be measured on a 1 cm$^3$ sample of the bone graft.

The graft may have a surface area, where the human cadaveric bone material may be at least 50%, at least 60%, at least 70%, at least 80%, or at least 90% of the surface area in embodiments. The bone material may be considered in the polymeric binder even though bone material is exposed at a surface. Bone material exposed at a surface may still be adjacent to the polymeric binder and may be immobilized by the formation of the polymeric binder next to the bone material.

Bone grafts may include fibers, including muscle fibers and other human fibers.

In another aspect, embodiments of the present technology include a method of making a bone composite. The method may include adding a liquid to a plurality of human cadaveric particles to form a wet mixture. The liquid may include a plurality of monomers. The method may also include compacting the wet mixture to form a compacted wet mixture. The method may further include polymerizing the plurality of monomers to form a solidified polymer. The method may also include immobilizing the plurality of human cadaveric bone particles in the solidified polymer to form the bone composite.

The solidified polymer may or may not bond with the bone particles. In some embodiments, the liquid with a plurality of monomers may fill in voids and spaces between bone particles, and then the formation of a solid polymer around the particles may immobilize the bone particles. PMMA may be an example of a polymer that immobilizes the bone particles in this manner. PMMA may entrap bone particles without chemical bonding between the PMMA and the bone particles. In other embodiments, polymers may bond with bone particles at a molecular level. For example, cyano acrylate may bond with bone particles.

The wet mixture may also include a plurality of polymer particles. The polymer particles may include a polymer formed by polymerizing monomers of the same molecular formula as the monomers in the plurality of monomers. For example, the monomer may be methyl methacrylate (MMA), and the polymer particles may include polymethyl methacrylate (PMMA). The plurality of monomers and the plurality of polymer particles may constitute two parts of a formula for bone cement. In some embodiments, the method may include mixing the plurality of polymeric particles with the human cadaveric bone particles before adding the liquid.

The wet mixture may not include a plurality of polymer particles. For example, the wet mixture may not include any polymethyl methacrylate particles. The weight ratio of the plurality of polymer particles to the plurality of monomers in the wet mixture may be less than 3:1. For example, the weight ratio may be less than 70:30, less than 60:40, less than 50:50, less than 40:60, less than 30:70, less than 20:80, or less than 10:90.

The liquid may be at a temperature less than 60° F., less than 50° F., less than 40° F., or less than 30° F. according to embodiments. The polymer particles and/or the bone particles may be at a temperature less than 60° F., less than 50° F., less than 40° F., or less than 30° F. according to embodiments.

The method may also include polymerizing the plurality of monomers within 10 minutes, 7 minutes, 5 minutes, 4 minutes, or 3 minutes of adding the liquid.

The method may also include ablating the bone composite after immobilizing. Ablating the bone composite may include sanding or machining the bone composite. Ablating the bone composite may increase the surface area of the exposed bone particles.

In a further aspect, embodiments of the present technology include a method of making a bone composite. The method may include densifying a plurality of human cadaveric bone particles to form a densified plurality of human cadaveric bone particles. Densifying the plurality of human cadaveric bone particles may include densifying a plurality of polymer particles. Densifying the plurality of polymer particles may include centrifuging or applying negative pressure.

The method may also include adding a liquid to the compacted plurality of human cadaveric bone particles. The liquid may include monomers. The liquid may be added to the compacted plurality of human cadaveric bone particles with as fast a flowrate as possible. Polymerization may begin soon after monomers contact polymer particles.

The method may also include mixing a plurality of human cadaveric bone particles with a plurality of polymer particles before densifying. The polymer particles may include a polymer formed by polymerizing monomers of the same molecular formula as the monomers in the liquid.

The method may further include exposing the densified plurality of human cadaveric bone particles to a negative pressure before adding the liquid. For example, the human cadaveric bone particles may be exposed to a vacuum. The negative pressure may be applied while adding the liquid to the plurality of human cadaveric bone particles.

The method may further include polymerizing the monomers to form a solidified polymer. The method may also include immobilizing the plurality of human cadaveric bone particles in the solidified polymer to form the bone composite.

In yet another aspect, embodiments of the present technology may include a method of treating a bone defect in a human patient. The method may include applying a bone graft to a treatment site of the human patient. The bone graft may include human cadaveric bone particles and a polymeric binder. The bone graft may be any bone graft or bone composite described herein.

The bone defect may be a fracture, a disease, an infection, a void, or a genetic abnormality. The treatment site may be in the foot. For example, the bone graft may supplement or replace a navicular bone. Bone grafts may also supplement or replace spine (vertebrae), bones in the hand, bones in the foot, ribs, or facial bones.

DETAILED DESCRIPTION

Embodiments of the present technology may bond together bone particles with a polymeric binder to form a bone graft or composite for implantation in a patient. Embodiments include grafts and methods of making composites that would use otherwise discarded bone particles. Embodiments may involve grafts or composites with consistent properties similar to natural bone. What is more, processing parameters and composition parameters may be adjusted to affect the properties of the graft or composite.

Conventional technologies do not provide the advantages of embodiments of the present technology. Simply mixing polymeric binder and bone particles may not provide a bone graft with consistent and desirable properties. For example, mixing a polymeric binder and bone particle may produce a mixture with properties similar to bread dough. This mixture may have voids and air pockets within the mixture, and the mixture may not harden to form a composite with sufficient mechanical integrity to replace or supplement natural bone. Other conventional technologies may include synthetic composites, which may not have the flexibility of natural bone and may disintegrate under stress that normal bone can withstand. Furthermore, synthetic composites, without natural bone present on its surface, may not facilitate the growth of natural bone on the composite and may not integrate in a patient's body as well as embodiments of the present technology.

Figure 1:
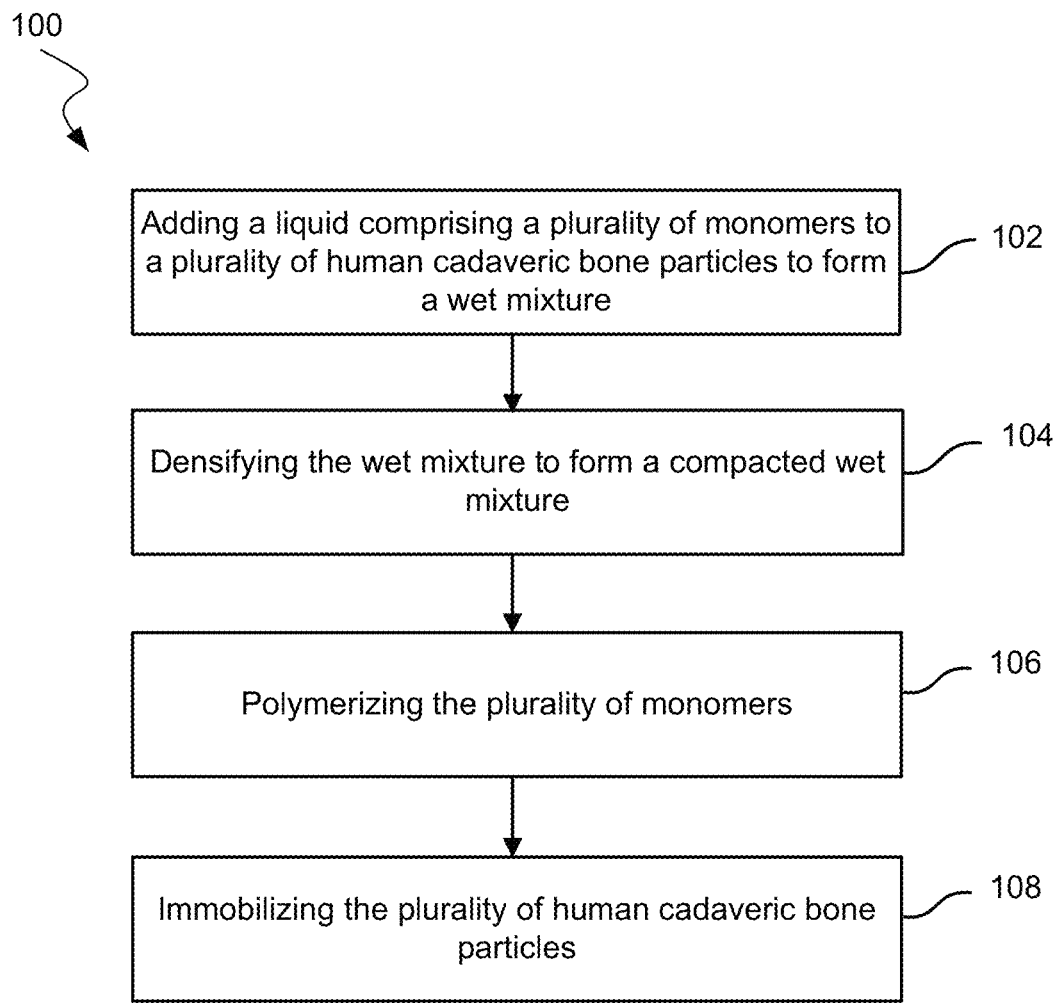
FIG. 1 shows a block flow diagram of a method of making a bone composite according to embodiments.

Turning to the figures, FIG. 1 shows a block flow diagram of a method 100 of making a bone composite according to embodiments. Method 100 may include adding a liquid with a plurality of monomers to a plurality of human cadaveric bone particles to form a wet mixture 102. Mixing the liquid and bone particles together may form a wet mixture that has a soft, doughy consistency. Method 100 may also include compacting the wet mixture to form a compacted wet mixture 104. Compacting the wet mixture may include packing the wet mixture into a container, such as a centrifuge tube. Compacting the wet mixture may include spincasting or centrifuging the wet mixture, which may compact the particles and/or incorporate monomers in the voids between the particles. The centrifugation forces used can reach 100,000×g.

Method 100 may further include polymerizing the plurality of monomers 106 to form a solidified polymer. Also, method 100 may include immobilizing the plurality of human cadaveric bone particles 108 in the solidified polymer to form the bone composite. Without the polymer to act as a binder, the human cadaveric bone particles may otherwise not be immobilized or stick together. The binder may or may not physically or covalently bond with the bone particles. The bone composite may be any graft described herein. Additionally, the monomer, bone particle, and polymer may be any monomer, bone particle, and polymer described herein.

Figure 2:
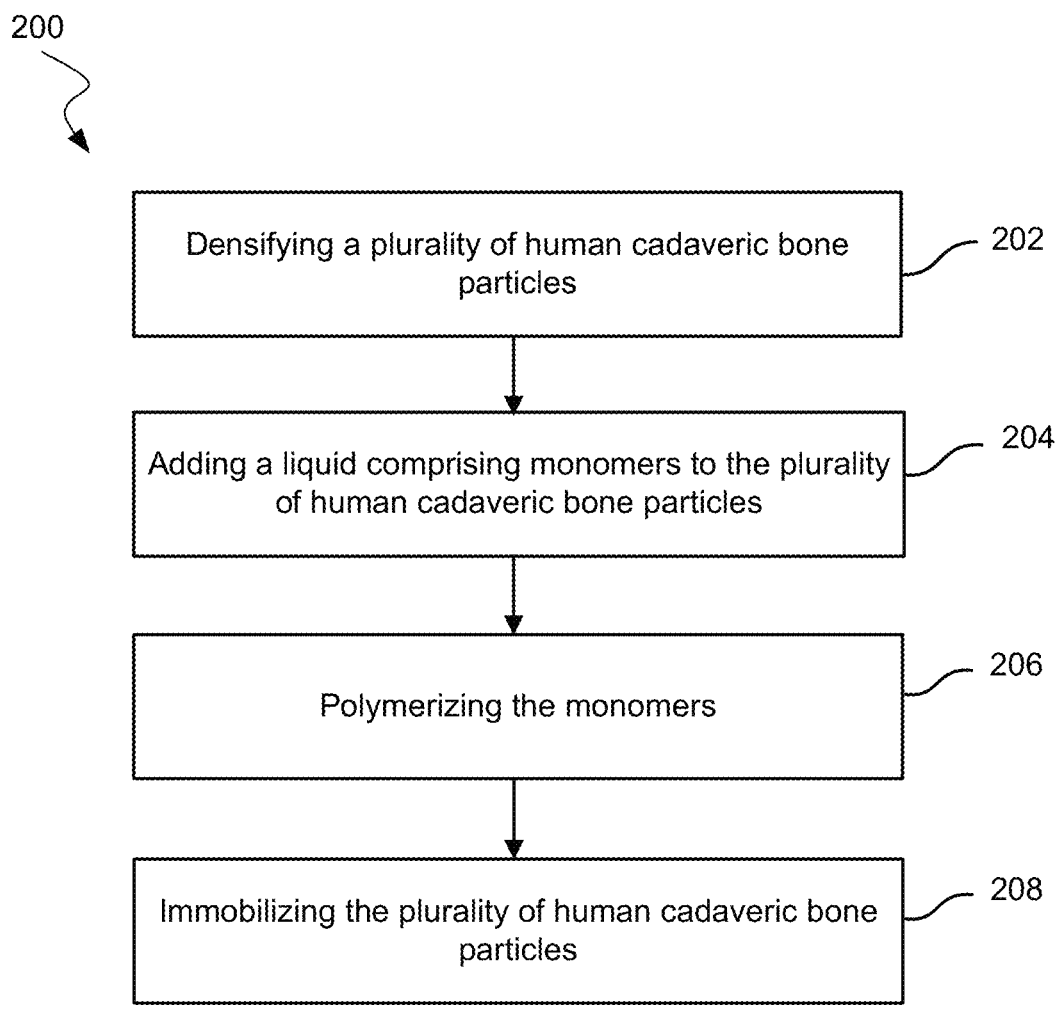
FIG. 2 shows a block flow diagram of a method of making a bone composite according to embodiments.

Turning to FIG. 2, this figure shows a block flow diagram of a method 200 of making a bone composite. Method 200 may include densifying a plurality of human cadaveric bone particles 202. Also, method 200 may include adding a liquid comprising monomers to the plurality of human cadaveric bone particles 204. The method may further include polymerizing the monomers 206 to form a solidified polymer. Additionally, method 200 may include immobilizing the plurality of human cadaveric bone particles 208 in the solidified polymer to form the bone composite. The bone composite may be any graft described herein. Additionally, the monomer, bone particle, and polymer may be any monomer, bone particle, and polymer described herein.

Methods and bone grafts may exclude cross-linking polymers. Cross-linking polymers may often involve cross-linking agents. Cross-linking agents may not be desired in the final bone graft and may be difficult to remove if used to cross link polymers.

Method 200 may differ from method 100 in the order the liquid is added and the particles are densified or compacted. In method 200, the liquid may be added after initially densifying the plurality of human cadaveric bone particles, while in method 100, the liquid may be added before compacting the particles. Method 200 may also include further densification after liquid is added. Method 200 may be controllable and repeatable and may not form an intermediate mixture with too low a density.

Bone grafts and methods of forming bone composites and may involve different ratios of bone and binder. Different ratios may affect the strength and appearance of the final product. Bone may be stronger than binder. A higher ratio of bone may result in a stronger composite, at least initially. The ratio may eventually become too large, with not enough binder to bond the bone material together.

Likewise, different ratios of polymer to monomer may be used in methods of making bone composites. The ratio of the polymer powder, such as PMMA, to liquid monomer, such as MMA, may range from 0:100 to 75:25. The ratio may affect the strength and synthetic content of the final product. Without any polymer particles initially with the bone particles, the liquid monomer may be able to more effectively eliminate space in the bone particles. However, the lack of polymers in the bone particles may reduce the amount of polymerization of the monomer. Thus, decreasing the ratio of polymer to monomer may then decrease the spaces or voids between bone particles but may also decrease the amount of polymerization. This trade off would affect the strength of the final composite. Ratios may also impact setting time, hardening time, and temperature during the process. The polymerization may be exothermic, and hence the degree of polymerization may affect the heat generated in the process.

The setting and hardening times may be affected by the temperature of the materials and the ambient environment. The liquid monomer, the bone particles, and/or the polymer particles may be cooled in order to increase the setting and hardening times.

Figure 3:
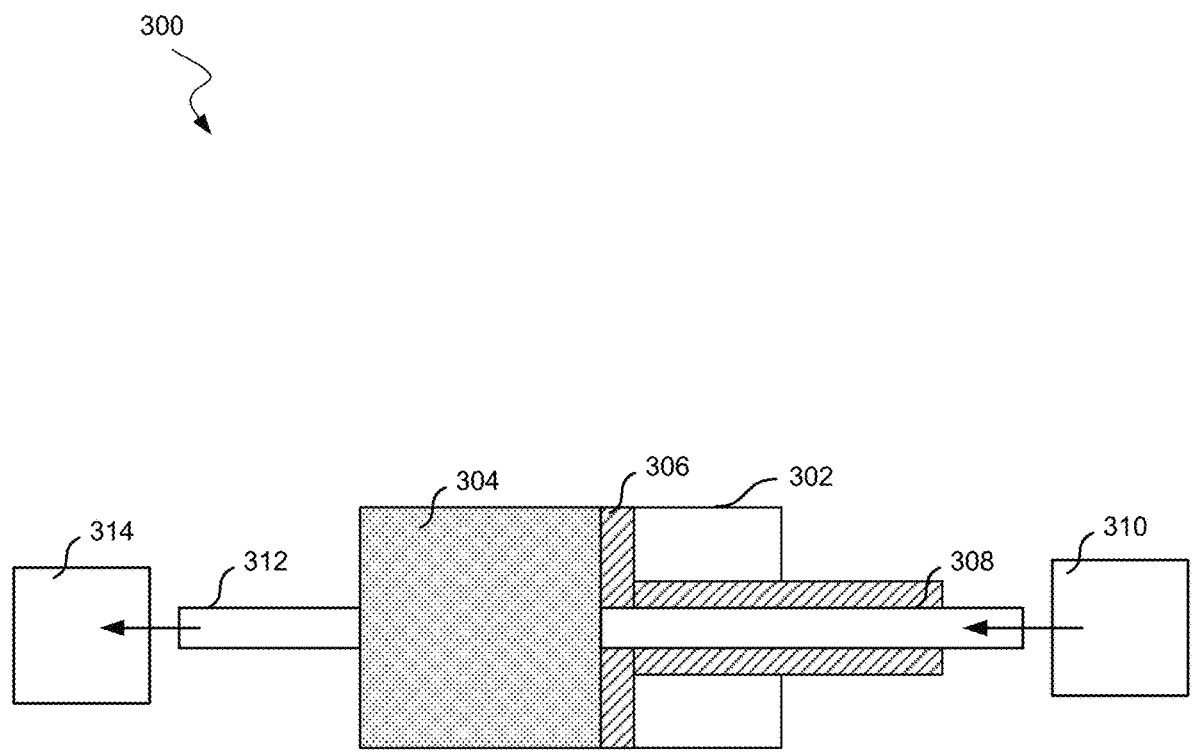
FIG. 3 shows a system 300 for making bone composites according to embodiments.

Turning to FIG. 3, system 300 may be used to make bone composites by method 200. System 300 may include a reservoir 302. Reservoir 302 may be a cylinder or part of a syringe. Reservoir 302 may hold a plurality of particles 304. Particles 304 may include bone particles and optionally polymer particles. A translatable partition 306 may move along the reservoir and against particles 304, resulting in decreased voids or smaller voids between particles 304. Translatable partition 306 may be a plunger of a syringe. Translatable partition 306 may compact or densify particles 304. Translatable partition 306 may define an aperture 308, with one end of aperture 308 open to particles 304. The other end of aperture 308 may be open to a fluid source 310. In this manner, a fluid from fluid source 310 may be delivered to particles 304. Fluid source 310 may include monomers and/or a solvent. Aperture 308 may also be defined by plastic, metal, or other tubing. The end of reservoir 302 opposite aperture 308 may include a channel 312. Channel 312 may be defined by plastic, metal, or other tubing. Channel 312 may be attached to a pump 314. Pump 314 may create a vacuum or negative pressure in reservoir 302, specifically in the area that contains particles 304. This negative pressure may densify particles 304 and/or draw fluid from fluid source 310, through aperture 308, and into voids in particles 304. The size of channel 312 or a filter in reservoir 302 may prevent particles 304 from exiting reservoir 302 or channel 312 and into pump 314.

System 300 and method 200 may be combined with a method similar to method 100. For example, system 300 may be included in a centrifuge. Centrifuging may densify particles 304. Densifying by centrifuging may occur before or during the addition of fluid to particles 304.

Figure 4:
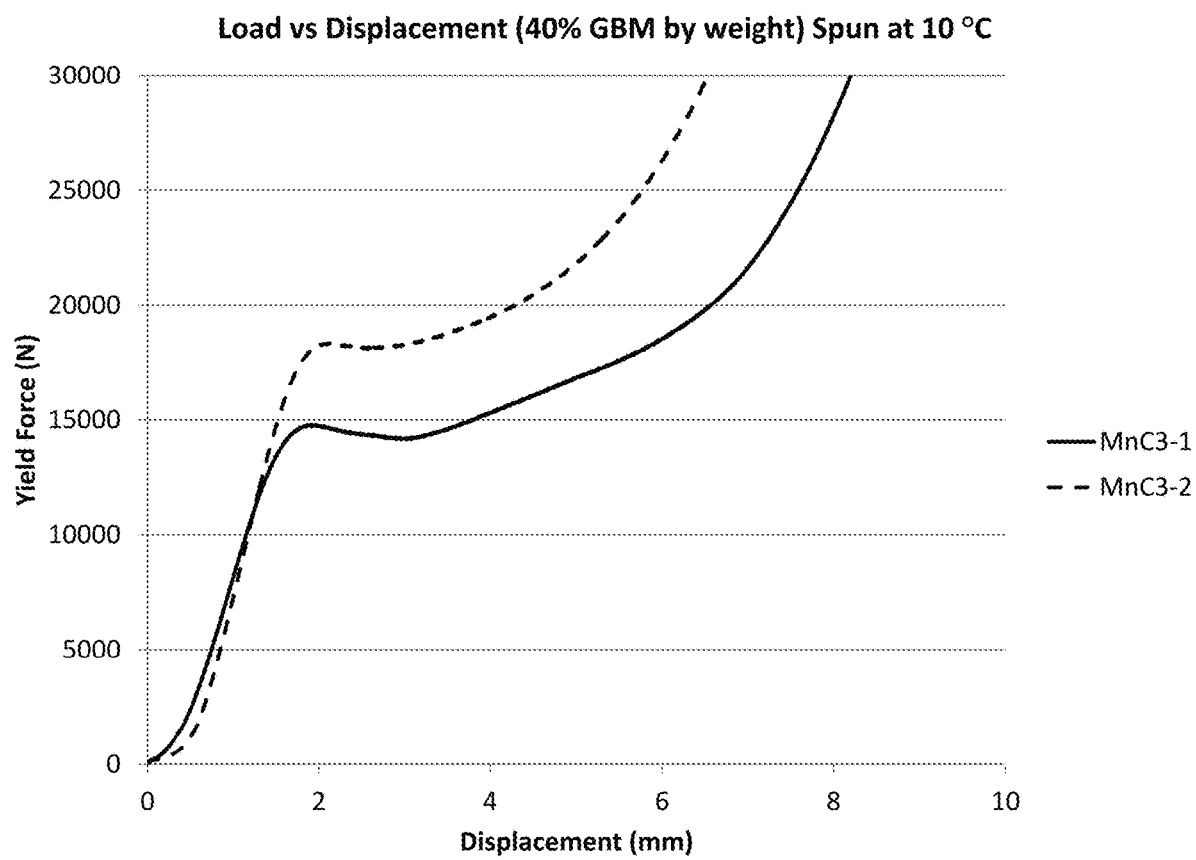
FIG. 4 is a graph of load versus displacement for a bone composite according to embodiments.

FIG. 4 shows a graph of load versus displacement for a bone composite formed by mixing 40% ground bone matrix (GBM) with a polymethyl methacrylate binder. GBM is bone that has not been demineralized. The bone composite was formed with a spincasting method, which included centrifuging bone particles, polymer particles, and liquid monomer. A 1 $cm^3$ cube is subjected to compression testing to obtain the yield force (N) versus displacement (mm).

Figure 5:
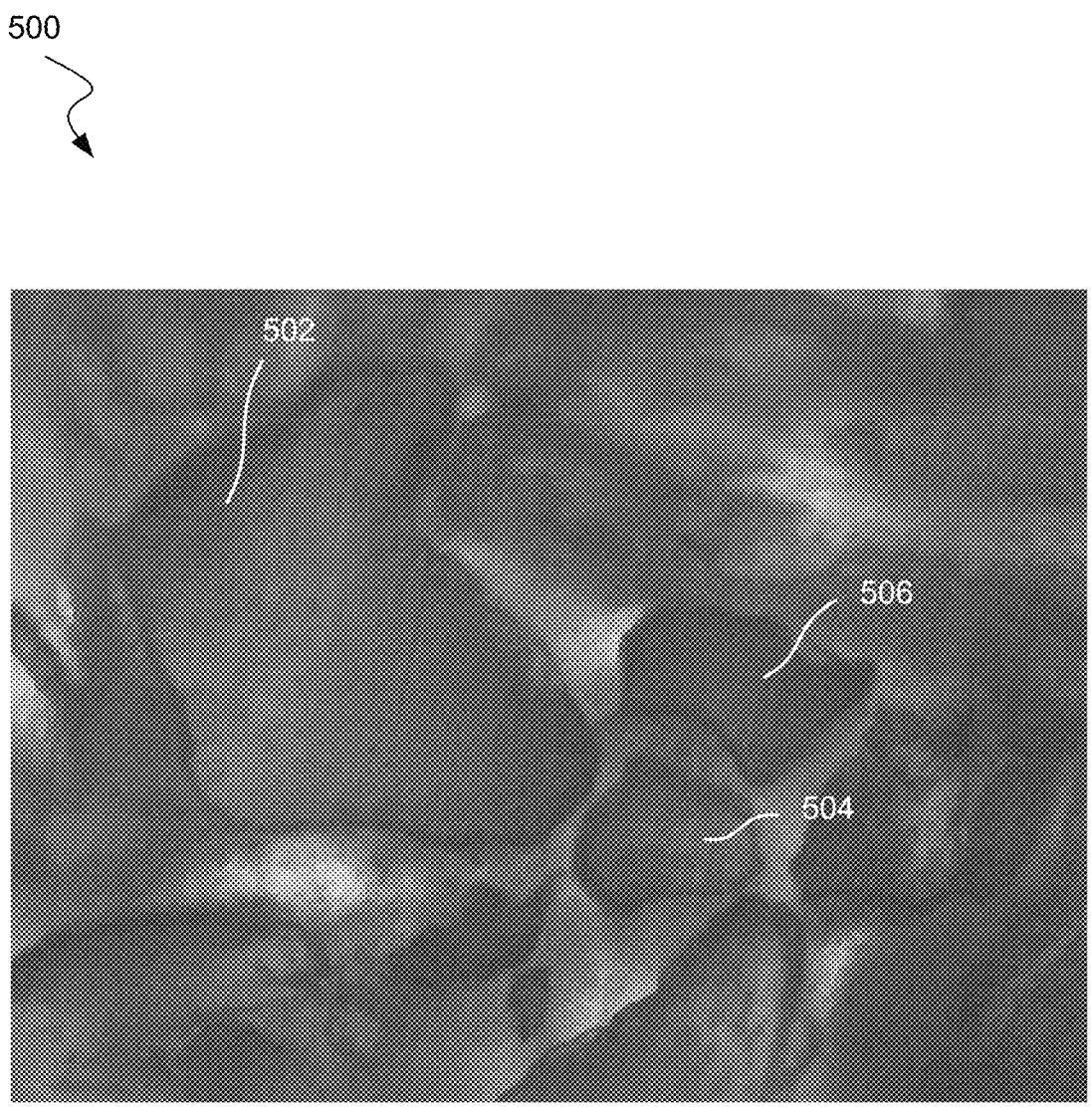
FIG. 5 is a microscope image of a slice of a bone composite according to embodiments.

Turning to FIG. 5, a picture 500 is shown of the surface of a 0.5 mm thick slice from a composite of 50 weight percent demineralized bone particles and 50 weight percent PMMA binder. Example demineralized bone particles are distinguishable as amorphous structures 502, 504, and 506. FIG. 5 shows over 55% of the surface area as demineralized bone particles. The more surface area that is demineralized bone, the more likely the bone composite may have superior results in the body of a human patient. Exposed bone material in a bone composite may allow for bone growth or may allow for increased compatibility in the body.

Bone Composites Via Spincasting (Spincast Human Bone Composites)

In some embodiments, the purpose of the development is to make a cadaveric human bone based structural graft that incorporates using a synthetic binder using centrifugation to create a strong long lasting bone based graft.

The development takes human cadaveric bone particles of specific sizes and combines with a synthetic binder. The ratio of each of the components is optimized to give the required strength of natural human bone, while minimizing the concentration of binder. The mixed components are then subjected to centrifugation forces to compact the particles with incorporation of the binder in the voids between the particles. The centrifugation forces used can reach 100,000× g.

To make human cadaveric bone particles into strong lasting implantable grafts using centrifugation.

The mode of operation is a structural graft that can withstand forces exerted by the human body. The content of the graft makes the graft mostly natural human bone which in theory can lead to better incorporation of the foreign graft into the host.

Bone particles do not stick together without the aid of a medium. To make a composite of bone that can withstand high levels of pressure and stress, the medium has to be substantially strong.

One such medium is cyano acrylate (Super Glue®) which is currently used as surgical glue in humans that the body dissolves over a time. In this method the medium is used at its lowest possible concentration to yield the strength similar to human bone.

Other similar embodiments may include applying vacuum or chemically modifying the tissue to make it bind together. The method of using centrifugation (spincasting) to make the structure makes the application different.

Human cadaveric bone is harvested and then section cleaned of soft tissue and bodily fluids. It is next ground into particles that are less than 1.1 mm. The particles are then cleaned and demineralized via a proprietary method. The ground bone is then vacuum dried. From here the bone is used as is (Demineralized Bone Matrix-DBM) or is further ground to less the 250 microns to make a powder (Demineralized Bone Powder-DBP). The binder component is currently cyano acrylate (Super Glue®) and could be replaced with a number of other biocompatible synthetic glues.

The components, DBP, DBM, and binder are weighted out and combined then mixed and placed in a centrifuge tube. The tubes are then centrifuged at high rpm to compress the particles and to extrude any excess fluid to the top. The centrifugation is run long enough to allow for the glue to set and then allowed to cure completely. Next the contents are extracted. The solidified plug is then machined via CNC into its final configuration.

There are other glues that can be used as a binder.

Currently initial prototypes of compressed structures have been made with bone and cyano based glue and currently testing compression strength of different combinations. Prototypes have also been machined to evaluate how the formulation behaves during shaping.

Polylactic Acid (PLA) Coated Bone Particles

In further embodiments, the purpose of development is to make a bone based powder that is coated with PLA to give the particles a binder for adhesion.

The development takes bone particles of any size and coats the outer surface either partially or completely. With the addition of PLA to the surface of the particle, it now has a glue/binder that can be heated to cause the PLA to melt and form a solid.

To make bone particles moldable into strong long lasting configurations.

The PLA coated particles can be molded into a shape and then the mold heated to melt the PLA and get a solid, slowly dissolved (months) structure that can support substantial forces and stress.

Bone particles do not stick together without the aid of a medium. To make a composite of bone that can withstand high levels of pressure and stress the medium has to be substantially strong. One such medium is PLA (polylactic acid) and it is used as a human implant material that the body dissolves over a long period of time. In this method the PLA is dissolved and then combined with bone particles and subsequently treated to cause the PLA to solidify out of solution onto the surface of the bone particles/powder.

The product is made by obtaining clean and sterile bone particles/powder and then dissolving amorphous PLA in glacial acetic acid and combining the bone and the PLA solution to a dough consistency and no excess fluid. The dough mixture is then mixed with sodium bicarbonate to homogeneity. The mixture is then exposed to water for injection (WFI) to cause a twofold reaction, one, the acetic acid combines with the sodium bicarbonate and forms $CO_2$ gas, water, and Na ions, therefore neutralizing the acetic acid. Second, the introduction of water causes the PLA to precipitate on the surface of the bone particles. The mixture is allowed to convert the acetic acid to gas and water and then the mixture is washed followed by lyophilization.

Structural Bone Graft Composites

In yet further embodiments, the purposed of the development is to make a cadaveric human bone based structural graft that incorporates using human cadaveric fibers, human cadaveric proteins, and a synthetic binder using isostatic pressure to create a strong long lasting bone based graft.

The development takes human cadaveric bone particles of specific sizes and combines with human cadaveric collagen fibers and a synthetic binder. The ratios of each of the components are optimized to give the required strength of natural human bone, while minimizing the concentration of binder. The mixed components are then subjected to an initial compaction to reduce the volume and then subjected to isostatic pressures (up to 66,000 psi), followed by a curing at elevated temperature for a specified time and then cooled. After cooling the graft can be shaped mechanically into its final configuration.

To make human cadaveric bone particles into strong long lasting configurations using isostatic pressing.

The mode of operation is as a structural graft that can withstand forces exerted by the human body. The content of the graft makes the graft mostly natural human tissue which in theory can lead to better incorporation of the foreign graft into the host.

Bone particles do not stick together without the aid of a medium. To make a composite of bone that can withstand high levels of pressure and stress the medium has to be substantially strong. One such medium is PLA (polylactic acid) which is currently used as a human implant material that the body dissolves over a long period of time. In this method the medium is used at its lowest possible concentration to yield the strength similar to human bone.

Human cadaveric bone is harvested and then section cleaned of soft tissue and bodily fluids. It is next, ground into particles that are less than 1.1 mm. The particles are the cleaned and demineralized via a proprietary method. The ground bone is then vacuum dried. From here the bone is used as is (Demineralized Bone Matrix-DBM) or is further ground to less than 250 microns to make a powder (Demineralized Bone Powder-DBP). Fibers for this project were obtained from a variety of sources by ultimately used muscle fibers because muscle is abundant during a recovery of other tissues. The muscle is cut into ~3-8 cm³ cubes and homogenized with saline solution. The homogenized muscles is then freeze dried. Once dry the muscle is pulverized and sieved over a 1 mm sieve. The retained fibers are collected. The fibers >1 mm are then treated with 3-6% hydrogen peroxide and washed with saline. The remaining fibers are then vacuum dried. Once dried they are untangled and used as is. The binder component is currently polylactic acid and could be replaced with a number of other biocompatible synthetic plastics or glues.

The four components, DBP, DBM, fibers, and binder are weighed out and combined then mixed and placed in a cylindrical mold. A plunger is inserted and then pressed using a hydraulic press to 15,000 to 18,000 psi for approximately 5 minutes, next the pressed plug is removed from the mold and placed in a foam mold and sealed. The sealed mold is then inserted into the isostatic press and subjected to up to 66,000 psi for a specific time. Once the time has elapsed the mold is pulled out the isostatic press and extracted from the mold. The pressed plug is then placed in a compression device and pressed and heated for a specific amount of time at a specific elevated temperature (>50° C.). After the heating the compression device is removed from the oven and cooled to room temperature and the plug is extracted. The plug is then shaped into a final configuration using a CNC system with specific tooling.

Currently initial prototypes of compressed structures have been made with the four components and currently testing compression strength of different combination. Prototypes have also been machined to evaluate how the formation behaves during shaping.

Embodiments of the present technology can be better understood by the following examples.

EXAMPLE 1

To determine mechanical properties of bone composites, a 1 cm³ cube is machined from a casted bone composite. The cube is compressed and the yield force is measured. With returning reference to FIG. 4, the results for two different samples of a composite of 40 weight percent ground bone matrix are shown. The results for one sample are indicated by the solid line, and the results for another sample are indicated by the dashed line. The composite was made from spincasting a mixture of PMMA particles, bone particles, and MMA liquid monomer initially at 10° C.

The maximum yield strength can be determined from a local maximum point where the yield force stops increasing with displacement resulting from compression. With both these samples, the yield strength reaches a local maximum at around 2 mm of displacement. The compression modulus is determined by the slope of the curve in the linear portion of the graph before the local maximum. This example showed a repeatable and quantifiable method for measuring the mechanical properties of a bone composite.

EXAMPLE 2

The mechanical properties of several bone composites and other materials were tested in a manner similar to what was used in Example 1. Samples of demineralized bone material with a PMMA binder formed by spincasting were tested, including bone composites with 20%, 30%, 40%, 50%, and 66% demineralized bone material (DBM) by weight. Additionally, polyether ether ketone (PEEK), a thermoplastic polymer sometimes used as a bone graft or implant, is tested. Navicular bone, a bone in the foot that may be a candidate for a bone graft or implant, was also tested for comparison. The resulting compressive modulus (GPa) and yield strength (N) of these tests is shown in Table 1. In addition, the published result of cortical bone by D. T. Reilly and A. H. Burstein, "The Elastic and Ultimate Properties of Compact Bone Tissue," *J. Biomech.*, 8:393-405, 1975, was listed for comparison.

TABLE 1

Compressive Modulus and Yield Strength of Bone Materials

| Material | Compressive Modulus (GPa) | Yield Strength (N) |
|---|---|---|
| 20% DBM | 7.5 | 14,020 |
| 30% DBM | 7.8 | 15,090 |
| 40% DBM | 8.2 | 14,655 |
| 50% DBM | 8.0 | 13,430 |
| 66% DBM | 7.2 | 10,787 |
| PEEK | 3.5 | 9,500 |
| Navicular | 4.1 | 11,586 |
| Cortical bone | 17.9 | 20,500 |

As shown in Table 1, the demineralized bone material composites range in compressive modulus and yield strength. The bone composites have a higher compressive modulus and yield strength than PEEK. PEEK, while sometimes used as a bone graft or implant, may lack the flexibility of bone and may crush at certain pressures. The relatively lower properties in Table 1 provide quantified data behind the observations of PEEK. Navicular bone has a compressive modulus and yield strength greater than PEEK, indicating a higher flexibility than PEEK, but lower than the DBM bone composites tested. Cortical bone has a higher compressive modulus and yield strength than any bone composite or bone material tested.

This example shows that the compressive modulus and yield strength of a bone composite could be adjusted at least by varying the concentration of the DBM. This example also shows that the DBM bone composites can have similar mechanical properties to human bones and have superior mechanical properties compared to other materials used for bone implants.

EXAMPLE 3

The amount of surface area of a bone composite that is bone was analyzed. DBM particles were dyed with Coomassie Blue stain. After the DBM particles were dried, they were mixed with PMMA powder, and a 50 weight % DBM bone composite was made using a spincasting method. A 0.5 mm thick slice of the bone composite was shaved off and analyzed with a light microscope at 10× magnification. The resulting picture is shown in previously described FIG. 5.

The DBM particles are distinguishable as amorphous structures with blue outlines. Examples of DBM particles in FIG. 5 include particles 502, 504, and 506. Particles sizes of DBM in FIG. 5 range from 100 µm to 800 µm. FIG. 5 was analyzed for the amount of surface area taken by DBM. The DBM surface area was calculated to be 55.4%, and the binder surface area was calculated to be 44.6%.

This example shows that greater than 50% of the surface area of a composite may be bone material. This percentage may allow enough bone at the surface of the composite to integrate with native bone in the body of a patient.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the monomer" includes reference to one or more monomers and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A method of making a bone composite graft for administration to a patient, the method comprising:
    combining a human cadaveric bone material with a plurality of polymethyl methacrylate binder particles;
    spincasting the combined human cadaveric bone material and polymethyl methacrylate binder particles to produce the bone composite graft, and
    ablating the bone composite graft to increase the surface area of bone material exposed,
    wherein the human cadaveric bone material is immobilized in the plurality of polymethyl methacrylate binder particles,
    wherein the human cadaveric bone material is present in an amount that is 50 weight percent of the bone composite graft, or less, and
    wherein the bone composite graft has a yield strength that is at least 13,000 N/cm2 and no greater than 15,000 N/cm2.

2. The method of claim 1, wherein the human cadaveric bone material comprises demineralized bone particles.

3. The method of claim 2, wherein the demineralized bone particles have an average diameter less than 1.1 mm.

4. The method of claim 2, wherein the demineralized bone particles have an average diameter less than 250 μm.

5. The method of claim 1, wherein the bone composite graft has a compressive modulus that is at least 7.5 GPa and no greater than 8.2 GPa.

6. The method of claim 1, wherein the bone composite graft has a surface area, and at least 50% of the surface area is the human cadaveric bone material.

7. The method of claim 1, wherein the human cadaveric bone material is present in an amount within a range from 20 weight percent of the graft to 50 weight percent of the bone composite graft.

8. The method of claim 1, wherein the human cadaveric bone material is present in an amount within a range from 20 weight percent of the graft to 40 weight percent of the bone composite graft.

9. The method of claim 1, wherein the human cadaveric bone material is present in an amount that is 30 weight percent of the bone composite graft.

10. The method of claim 1, wherein the human cadaveric bone material comprises demineralized bone material.

11. The method of claim 1, wherein the bone composite graft has a surface area, wherein a percentage of the surface area is the human cadaveric bone material, wherein the human cadaveric bone material is present in an amount that is a weight percent of the bone composite graft, and wherein the percentage of the surface area that is human cadaveric bone material is greater than the weight percent.

12. The method of claim 11, wherein the percentage of the surface area that is human cadaveric bone is greater than 50 percent and no more than 56 percent, and the weight percent is 50 weight percent.

13. The method of claim 1, wherein the bone composite graft has a surface area, wherein a percentage of the surface area is the human cadaveric bone material, wherein the human cadaveric bone material is present in an amount that is a weight percent of the bone composite graft, wherein the percentage of the surface area that is human cadaveric bone is 55.4 percent and the weight percent is 50 weight percent.

14. The method of claim 1, wherein the bone composite graft consists of the human cadaveric bone material and the polymethyl methacrylate, and wherein the human cadaveric bone material is present in an amount that is 50 weight percent of the bone composite graft, or less.

15. The method of claim 1, wherein the human cadaveric bone material and the plurality of polymethyl methacrylate binder particles are densified following the spincasting step.

16. The method of claim 15, wherein the plurality of polymethyl methacrylate binder particles are present as a densified powder following the spincasting step.

17. A method of making a bone composite graft for administration to a patient, the method comprising:
    combining a human cadaveric bone material, an amount of muscle fibers, and a polymeric binder; and
    compressing the combined human cadaveric bone material, muscle fibers, and polymethyl methacrylate binder particles to produce the bone composite graft,
    wherein the human cadaveric bone material and the amount of muscle fibers are immobilized in the polymeric binder.

18. The method of claim 17, wherein the polymeric binder comprises polylactic acid.

19. The method of claim 17, wherein the binder comprises a biocompatible synthetic plastic.

20. The method of claim 17, wherein the binder comprises a biocompatible synthetic glue.

21. A method of making a bone composite graft for administration to a patient, the method comprising:
    combining a plurality of human cadaveric bone particles with a plurality of polymethyl methacrylate binder particles;
    spincasting the combined human cadaveric bone particles and polymethyl methacrylate binder particles to produce the bone composite graft, and
    ablating the bone composite graft to increase the surface area of bone material exposed,
    wherein the plurality of human cadaveric bone particles are immobilized in the plurality of polymethyl methacrylate binder particles.

22. The method of claim 21, wherein the human cadaveric bone particles comprise demineralized bone particles.

23. The method of claim 22, wherein the demineralized bone particles have an average diameter less than 1.1 mm.

24. The method of claim 22, wherein the demineralized bone particles have an average diameter less than 250 µm.

25. The method of claim 21, wherein the bone composite graft has a compressive modulus that is at least 7.5 GPa and no greater than 8.2 GPa.

26. The method of claim 21, wherein the bone composite graft has a surface area, and at least 50% of the surface area is the human cadaveric bone particles.

27. The method of claim 21, wherein the human cadaveric bone particles are present in an amount that is 50 weight percent of the bone composite graft, or less.

28. The method of claim 21, wherein the human cadaveric bone particles are present in an amount within a range from 20 weight percent of the bone composite graft to 50 weight percent of the bone composite graft.

29. The method of claim 21, wherein the human cadaveric bone particles are present in an amount within a range from 20 weight percent of the bone composite graft to 40 weight percent of the bone composite graft.

30. The method of claim 21, wherein the human cadaveric bone particles are present in an amount that is 30 weight percent of the bone composite graft.

31. The method of claim 21, wherein the bone composite graft has a yield strength that is from 13,000 N/cm2 to 15,000 N/cm2.

32. The method of claim 21, wherein the bone composite graft has a surface area, wherein a percentage of the surface area is the human cadaveric bone particles, wherein the human cadaveric bone particles are present in an amount that is a weight percent of the bone composite graft, and wherein the percentage of the surface area that is human cadaveric bone particles is greater than the weight percent.

33. The method of claim 32, wherein the percentage of the surface area that is human cadaveric bone is greater than 50 percent and no more than 56 percent and the weight percent is 50 weight percent.

34. The method of claim 21, wherein the bone composite graft has a surface area, wherein a percentage of the surface area is the human cadaveric bone material, wherein the human cadaveric bone particles are present in an amount that is a weight percent of the bone composite graft, wherein the percentage of the surface area that is human cadaveric bone particles is 55.4 percent and the weight percent is 50 weight percent.

35. The method of claim 21, wherein the bone composite graft consists of the human cadaveric bone particles and the polymethyl methacrylate, and wherein the human cadaveric bone particles are present in an amount that is 50 weight percent of the bone composite graft, or less.

36. The method of claim 21, wherein the plurality of human cadaveric bone particles and the plurality of polymethyl methacrylate binder particles are densified following the spincasting step.

37. The method of claim 21, wherein the plurality of polymethyl methacrylate binder particles are present as a densified powder following the spincasting step.

* * * * *